United States Patent [19]

Austin

[11] Patent Number: 5,078,600

[45] Date of Patent: Jan. 7, 1992

[54] MULTIFUNCTION MANDIBULAR MOVEMENT MEASURING DEVICE

[76] Inventor: David G. Austin, 4210 Rowanne Rd., Columbus, Ohio 43214

[21] Appl. No.: 542,966

[22] Filed: Jun. 25, 1990

[51] Int. Cl.⁵ .............................................. A61C 19/04
[52] U.S. Cl. ......................................... 433/73; 433/69
[58] Field of Search ............... 433/73, 68, 69; 33/513, 33/514

[56] References Cited

U.S. PATENT DOCUMENTS

| | | | |
|---|---|---|---|
| 1,023,542 | 4/1912 | Winter | 433/73 |
| 1,044,206 | 11/1912 | Little | 433/68 |
| 1,052,806 | 2/1913 | Evans | 433/73 |
| 1,497,259 | 6/1924 | Bonoff | 433/73 |
| 1,589,802 | 6/1926 | Gould | 433/73 |
| 1,662,670 | 3/1928 | Harter | 433/73 |
| 1,674,088 | 6/1928 | Bodine | 433/73 |
| 3,336,670 | 8/1967 | Heydenreich | 433/73 |

Primary Examiner—John J. Wilson
Attorney, Agent, or Firm—Thomas S. Baker, Jr.

[57] ABSTRACT

A mandibular movement measuring device for measuring the angular movment of the mandibular incisal edge between the mandibular closed position and the maximum mandibular open position and for measuring mandibular deflection and deviation between the mandibular closed position and the maximum mandibular open position.

10 Claims, 2 Drawing Sheets

MULTIFUNCTION MANDIBULAR MOVEMENT MEASURING DEVICE

In order for doctors and/or dentists to properly diagnose the problems of some patients they must conduct an assessment of the patient's temporomandibular joint function. Based upon this assessment, some type of corrective action such as bite adjustment, split therapy or joint surgery including arthroscopy may be indicated or ruled out. Previously, there has been no universally accepted standard or standards for assessing temporomandibular joint function which accommodates skeletal variations and abnormalities in patients. Currently, dentistry assesses temporomandibular joint function simply by measuring the change in distance of the mandibular incisal edge between the mandibular closed position and the mandibular open position. In other words, they simply measure the distance or amount of opening between the front teeth on full opening of the mouth. In other branches of the medical profession, an examination of joint movement typically would be based upon the degree of angular movement of the joint members.

Angular movement as a basis of examining joint function provides a more meaningful determination of such function than mere distance measurement. In fact, a measurement of mandibular angular movement which accommodates incisive radius, this being the distance from the condyle or jaw joint to the mandibular central incisor, would provide a measurement of temporomandibular joint function which takes into account skeletal variations of subjects inasmuch as this radius determines the maximum interincisal opening.

Thus, it would be desirable to provide a device which enables a dentist or doctor to accurately measure the degree of mandibular angular movement developed by the change of position of the mandibular incisal edge between a mandibular closed position and a mandibular open position which takes into account the incisive radius. Additionally, it has been found desirable to provide a device which measures additional mandibular movements such as the amount of protrusion of the mandibular incisal edge which occurs when the mouth is open enough to allow forward movement of the lower jaw without tooth interference: a measurement of mandibular deflection which represents the final differential distance from the center or midline of the two maxillary and mandibular central incisors between closed and maximum opening positions; a measurement of mandibular deviation which represents the amount of lateral movement of the mandible from the centered position during normal opening of the jaw; a measurement of the maximum right and left lateral movements of the mandible from a centered position open enough to allow lateral movements of the lower jaw without tooth interference.

SUMMARY OF THE INVENTION

The instant invention provides a multifunction mandibular movement measuring device for measuring mandibular movements of a wearer having a mounting unit with a headband adapted to overlie the top portion of a wearer's head and a horizontal support adapted to rest against the face of the wearer. A measuring member having a probe for locating the mandibular incisal edge of a wearer is pivotally attached to the mounting unit to enable the measuring member to pivot downwardly with respect to the horizontal support. An angular measuring means for measuring angular movement of the measuring member developed by the change of position of the probe at the mandibular incisal edge between the mandibular closed position and the mandibular open position attaches to the mounting unit.

DESCRIPTION OF THE PREFERRED EMBODIMENT

Figure 1:
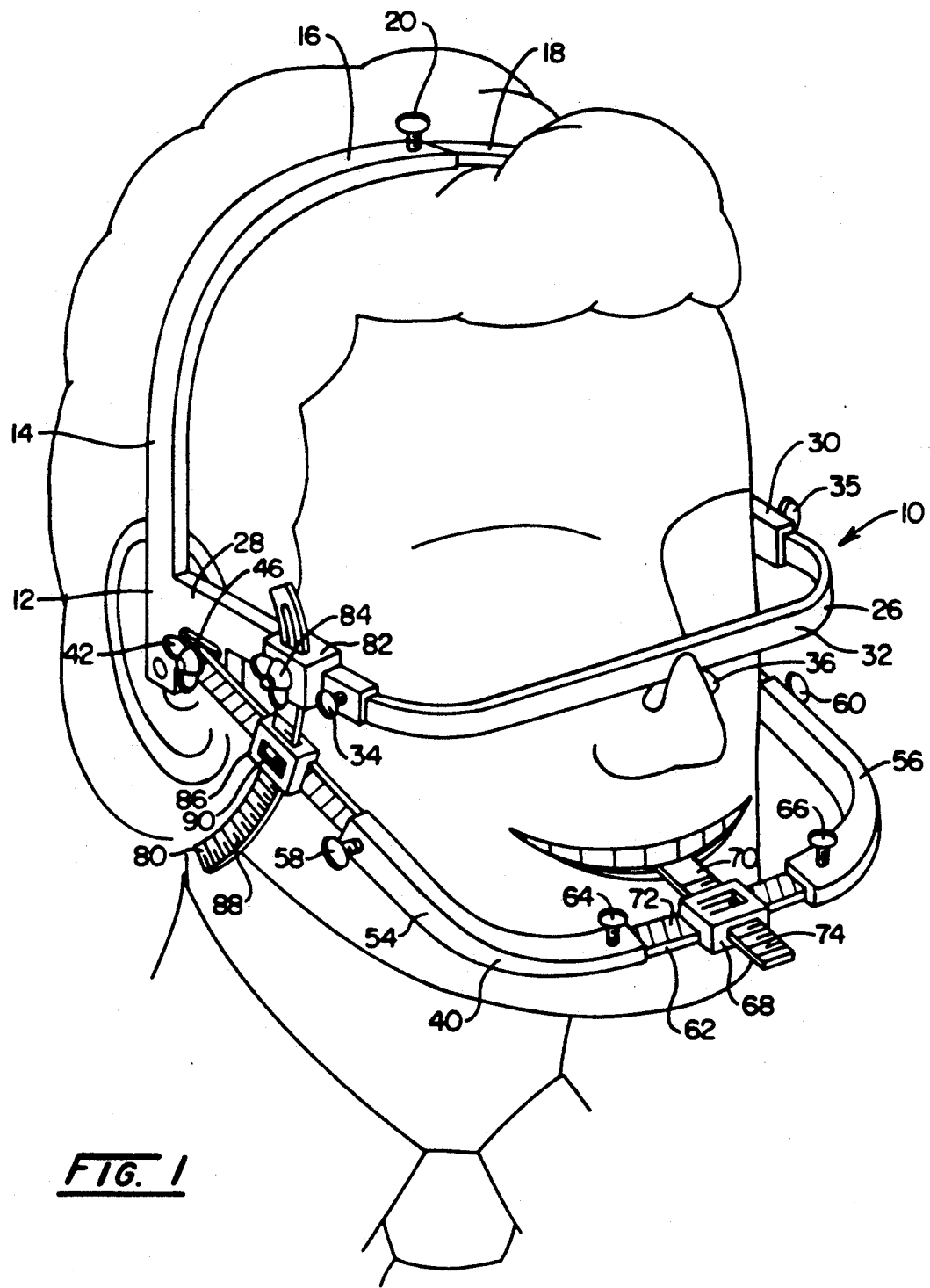
FIG. 1 is a perspective view of the multifunction mandibular movement measuring device of he present invention affixed to the head of a wearer.
Figure 3:
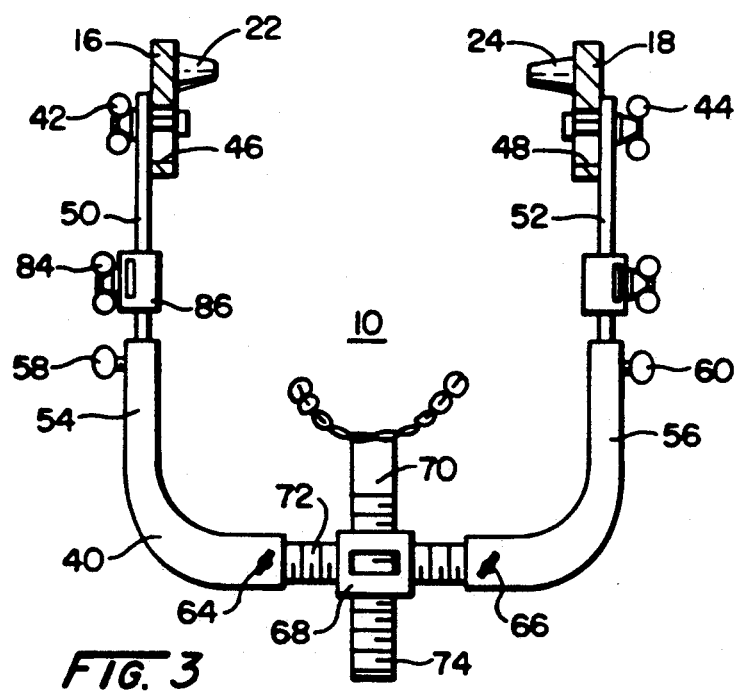
FIG. 3 represents a view along line 3—3 of FIG. 2.

Turning to FIG. 1, the multifunction mandibular movement measuring device (10) of the present invention may be seen mounted on the head of a wearer. The measuring device (10) has a mounting unit (12) which includes a U shaped headband (14) adapted to be worn over the head of the wearer. Headband (14) may be constructed out of metal or plastic and preferably has two concentric sliding pieces (16 and 18) one received within the other which may be slid towards each other to make the device fit tighter on the head of the wearer or slid apart to enlarge the opening. A thumb screw (20) locks the position of the sliding pieces (16 and 18) once the headband has been adjusted properly. Turning to FIG. 3, it may be seen that cone shaped ear pieces (22 and 24) are affixed to the lower ends of the sliding pieces (16 and 18) respectively. The ear pieces (22 and 24) are adapted to fit in the ears of the wearer to securely fit the mounting unit (12) on the head of the wearer. Turning again to FIG. 1, the mounting unit (12) further includes a horizontal support (26) adapted to overlie and rest against the face of the wearer. The horizontal support (26) has a pair of lateral side arms (28 and 30) connected to a front nose support (32). Nose support (32) is a U shaped bracket having a generally rectangular cross section and adapted to slide within channels formed within the lateral side arms (28 and 30). Clamp (34 and 35) secure the position of the front nose support (32). A nose piece (36) on front nose support (32) is adapted to rest upon the nose of the wearer.

Figure 2:
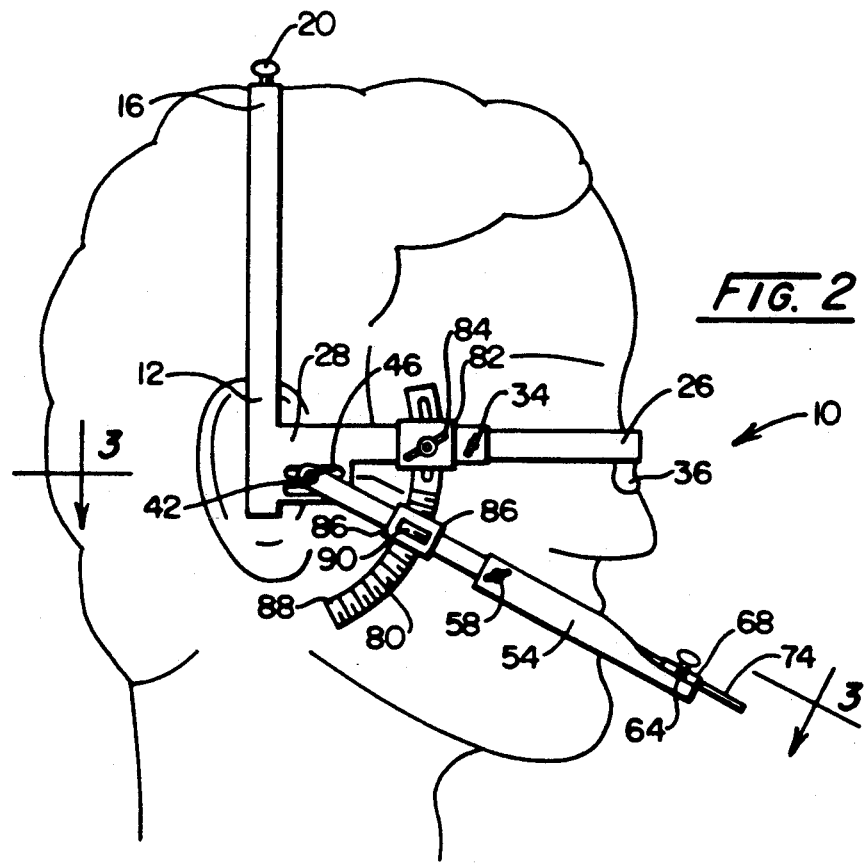
FIG. 2 is a side view of the multifunction mandibular movement measuring device of the present invention mounted on the head of a wearer.

From the above, it may be seen that the mounting unit (12) having a headband (14) which overlies the head of the wearer and may be adjusted to clamp against the wearer's head and securely locate ear pieces (22 and 24) within the ears of the wearer and a horizontal support (26 having a front nose support (32) which may be moved toward and away from the face of the wearer serve to securely mount the multifunction mandibular movement measuring device (10) upon the head of the wearer. Although the headband (14) has been illustrated as a single element formed at a right angle with respect to the horizontal support (26), it has been found that the headband (14) also may include two or more elements which overlie and rest against the head of the wearer. Regardless, the measuring device (10) has been found to be securely anchored to the head of the wearer with the embodiment described in connection with FIGS. 1 through 3.

The multifunction mandibular movement measuring device (10) has a U shaped measuring member (40) pivotally connected to the mounting unit (12). The measuring member (40) is pivotally mounted by a pair of thumb screws (42 and 44) which pass through holes, not shown, in each end thereof and projecting into lateral slots (46 and 48) formed just below the horizontal support (26). The slots (46 and 48) and thumb screws (42 and 44) enable the pivot axes of the U shaped measuring member (40) to be aligned with the lateral pole of the mandibular condyle position. This position may be determined by palpation of the patient or wearer. This position has been found to be an average of 10 mm anterior of the tragus of the ear. Thus, the slots (46 and 48) provide for anatomical variation of the lateral pole position.

Measuring arm (40) includes a pair of fixed arms (50 and 52) having one end which pivots about the thumb screws (42 and 44) respectively and an outer end adapted to be received within a pair of outer arms (54 and 56) respectively. Thumb screws (58 and 60) secure the outer arms (54 and 56) to the fixed arms (50 and 52) respectively. The ends of the outer arms (54 and 56) are connected by a relator control bar (62) adapted to be received within each of the arms (54 and 56). Thumb screws (64 and 66) serve to rigidly affix the relator control bar (62) to the outer arms (54 and 56).

A slide (68) rests upon relator control bar (62). Slide (68) has an opening which complements the outer surface of the control bar (62) to enable the slide (68) to move in a horizontal plane, i.e., side to side along the relator control bar (62). A relator probe (70) is mounted within openings within the slide (68) which enable the probe to slide fore and aft, i.e., toward and away from the mouth of the wearer while the slide (68) remains stationary on the relator control bar (62). The relator control bar (62) has distance measuring indicia (72) on the face thereof to provide a reading of the movement of the slide (68) from a center position. Similarly, the relator probe (70) has a distance measuring indicia (74) formed on the face thereof to provide an indication of the movement of the relator probe (70) with respect to the slide (68). A similar distance measuring indicia (76) may be found on the fixed arm (50) which may be utilized in conjunction with the distance measuring indicia (74) on the relator probe (70) to determine the incisive radius of a wearer as will be described hereinbelow.

A protractor (80) is slideably mounted in a sliding guide (82) which may be slid along the lateral side arm (28) of horizontal support (26). A thumb screw (84) locks protractor (80) and sliding guide (82) in position on fixed arm (50). Thumb screw (84) must be loosened to enable the guide (82) to slide whenever the thumb screws (42 and 44) are loosened to adjust the fixed arms (50 and 52) of the measuring member (40) within the slots (46 and 48). This procedure ensures that the protractor (80) remains a fixed distance from the pivot axis of the measuring member (40). The protractor (80) passes through openings formed in a slide (86) which in turn is slideably mounted on the fixed arm (50). Protractor (80) has an angular measuring indicia (88) formed on the face thereof. Preferably, a clear acrylic magnifying viewer (90) is mounted within the sliding guide (86) to make it easier for an operator to read the angular measuring indicia (88).

Operation of the multifunction mandibular movement measuring device (10) of the present invention will now be described. Initially, the device is adjusted such that the headband (14) overlies the top portion of a patient or wearer's head and the horizontal support (26) overlies the face of the wearer. The headband (14) is adjusted such that the ear pieces (24 and 26) rest in the wearer's ears and the headband (14) is clamped securely to the head of the wearer. The clamps (34 and 35) are loosened to adjust the front nose support (32) on the wearer such that nose piece (36) rests upon the central portion of the bridge of the wearer's nose. Thereafter the clamps (34 and 35) are tightened to secure the placement of the mounting unit (12) on the head of the wearer.

Thereafter, the lateral pole of each mandibular condyle position is ascertained and the thumb screws (42 and 44) are loosened to slide the fixed arms (50 and 52) of the U shaped measuring member (40) within the slots (46 and 48) until the thumb screws (42 and 44) about which the fixed arms pivot are axially aligned with the lateral poles. Subsequently, the incisive radius or the distance of the condyle pole to the mandibular incisor is ascertained. In order to make this measurement the measuring member (40) is rotated downwardly with respect to the horizontal support (26) until the relator probe (70) is aligned with the wearer's incisors, these being the central four teeth top and bottom of the wearer. The probe (70) is moved inwardly until the inner end engages the two inner incisors of the wearer as illustrated in FIG. 3. The incisive radius may be determined by adding the amount shown on the distance measuring indicia (72) of fixed ar (50) with the indication on the distance measuring indicia (74) on the relator probe (70). Alternatively, if the outer arms (54 and 56) are at a set distance on the fixed arms (50 and 52), the incisive radius may be read directly from a distance measuring indicia (74) on the relator probe (70). Preferably, the distance indicia (74) on the relator probe (70) would measure only the distance from the slide (68) and this sum would be added to the amount shown on the distance measuring indicia (76) on the fixed arm (50) to determine the incisive radius. This would enable the distance measuring indicia (74) on the relator probe (70) to be utilized for other measurements.

The mandibular movement measuring device (10) of the present invention provides an easy means for measuring the angular movement of the condyle by measuring the angle formed by the traveling of the incisal edge of the mandibular incisor between the mandibular closed position and the mandibular open position. To accurately take this angular measurement, the pivot axes of the fixed arms (50 and 52) of the U shaped measuring member (40) must be aligned with the lateral pole of the mandibular condyles. As mentioned previously, the thumb screws (42 and 44) may be loosened to slide the fixed arms (50 and 52) within the slots (46 and 48) to precisely align the thumb screws (42 and 44) with the lateral pole of the mandibular condyle on each side of the head of the wearer. During the time this measurement is made, the thumb screw (84) which fixes the position of the protractor (80) and the sliding guide (82) must be loosened to enable the protractor to slide along the fixed arm (50). After the thumb screws (42 and 44) have been located properly, the U shaped measuring member (40) must be pivoted downwardly to align the relator probe (70) with the mandibular incisal edge with the mouth in full closure. In this position, the protractor (80) must be moved in the sliding guide (82) until a zero angle reading appears in the window of the magnifying viewer (90). Thereafter, the wearer opens his mouth as wide as possible and the measuring member (40) is pivoted downwardly until the relator probe (70) again engages the mandibular incisal edge. This angular movement of the mandibular incisal edge between the mandibular closed position and the mandibular open position may be read directly in degrees from the measuring indicia (88) on the protractor (80).

Mandibular protrusion or the amount of forward movement of the lower jaw may be determined easily with the measuring device (10). Initially the relator probe (70) is positioned centrally on the relator control bar (62) to the center of the lower central incisors of the wearer. This position is read on the distance measuring indicia (72) on the relator probe (70). Next the wearer opens his mouth sufficiently to allow forward movement of the lower jaw without tooth interference and relator probe (70) is again brought in contact with the incisal edge of the lower central incisors subsequent to the wearer moving his jaw outwardly as far as possible. This new distance is read on the distance measuring indicia (72) of the relator probe. The difference in readings on the relator probe represents the protrusive movement distance.

Mandibular deflection and deviation may be read off the distance measuring indicia (72) on the relator control bar (62). Deflection represents the lateral distance the center of the wearer's lower two incisors moves laterally between the mandibular closed and the mandibular maximum open positions. The center of the lower two incisors may be measured by the distance measuring indicia (72) on the relator control bar (62) at the mandibular closed position and the mandibular maximum opening position and the difference between the two measurements will provide the amount of mandibular deflection. Lateral movement of the mandible from the centered position during normal opening of the jaw is deviation. Again, this distance may be read on the distance measuring indicia (72) of the relator control bar (62) as the relator probe (70) is moved between the centered positions during normal opening of the jaw.

Right and left lateral excursion of the mandible is the maximum lateral movement to the right or to the left of the mandibul from the center closed position which the wearer is capable of achieving. Again, these measurements may be determined by movement of the relator probe (70) and slide (68) along the distance measuring indicia (72) from the center or zero distance position to the maximum lateral movement positions.

The mandibular movement measuring device (10) of the present invention may be adapted to measure incisal opening directly. To make this measurement the relator probe (70) is slid out of the slide (68) and the amount of opening between the teeth is read.

From the above it may be seen that the multifunction mandibular movement measuring device (10) of the present invention provides an accurate measurement of mandibular movement including angle of opening, right and left incisive radii, protrusion, mandibular deflection and deviation, mandibular left and right lateral excursions and maximum opening. Because the measuring device may be adjusted such that the pivot axis coincides with the lateral pole of the mandibular condyle, the angle of opening of the wearer is accurately determined despite anatomical variations of the lateral pole position.

Since certain changes may be made to the above-described structure and method without departing from the scope of the invention herein it is intended that all matter contained in the description thereof or shown in the accompanying drawings shall be interpreted as illustrative and not in a limiting sense.

I claim:

1. A multifunction mandibular movement measuring device for measuring mandibular movements of a wearer which comprises:
    a mounting unit having a headband adapted to overlie the top portion of a wearer's head and a horizontal support adapted to rest against the face of a wearer;
    a measuring member having a probe for locating the mandibular incisal edge of a wearer;
    pivot means for pivotally attaching said measuring member to said mounting unit to enable said measuring member to pivot downwardly with respect to said horizontal support; and
    angular measuring means for measuring the angular movement of said measuring member developed by the change of position of said probe at the mandibular incisal edge between the mandibular closed position and the maximum mandibular open position.

2. The multifunction mandibular movement measuring device of claim 1 further comprising:
    probe mounting means for movably mounting said probe on said measuring member for movement toward and away from the mandibular incisal edge of the wearer; and
    probe readout means on said probe for stating the distance between said measuring member and the mandibular incisal edge of the wearer to determine the incisive radius of the wearer.

3. The multifunction mandibular movement measuring device of claim 2 further comprising:
    a relator control bar attached to said measuring member; and wherein said probe mounting means is mounted slidably on said relator control bar.

4. The multifunction mandibular movement measuring device of claim 1 further comprising:
    a relator control bar attached to said measuring member;
    probe mounting means for slidably mounting said probe for sideways movement on said relator control bar; and
    relator readout means for measuring lateral movement of said probe on said relator control bar to determine maximum mandibular deviation and deflection between the mandibular closed position and the maximum mandibular open position.

5. The multifunction mandibular movement measuring device of claim 4 further comprising:
    disconnect means for disconnecting said relator control bar from said measuring member to obtain the angle of maximum opening of the wearer.

6. The multifunction mandibular movement measuring device of claim 1 further comprising:
    lateral adjustment means on said mounting unit for adjusting said measuring member pivot means such that the pivot axis of said measuring member is coaxial with the wearer's condyle.

7. The multifunction mandibular movement measuring device of claim 6 further comprising:
    attaching means for attaching said angular measuring means to said mounting unit;
    wherein said attaching means includes adjustment means to adjust the distance of said angular measuring means from the wearer's condyle; and
    readout means attached to one said measuring member or said horizontal support for stating the maximum change in angle of the measuring member caused by the change of position of the probe.

8. The multifunction mandibular movement measuring device of claim 1 further comprising:
a pair of ear inserts mounted on said mounting unit and adapted to be placed in the ears of a wearer to assist in locating said movement measuring device on the head of said wearer.

9. The multifunction mandibular movement measuring device of claim 1 further comprising: adjustment means on said headband for adjusting the fit of said headband to the head of said wearer.

10. The multifunction mandibular movement measuring device of claim 1 in which:
said horizontal support has a pair of lateral sidearms and a front nose support member; and
side arm adjustment means mounted on said lateral sidearm for adjusting said horizontal support toward and away from the face of said wearer.

* * * * *